(12) United States Patent
Olson et al.

(10) Patent No.: US 9,592,100 B2
(45) Date of Patent: Mar. 14, 2017

(54) METHOD AND APPARATUS FOR ENCODING CATHETERS WITH MARKERS FOR IDENTIFYING WITH IMAGING SYSTEMS

(75) Inventors: Eric S. Olson, Maplewood, MN (US); John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1466 days.

(21) Appl. No.: 11/967,412

(22) Filed: Dec. 31, 2007

(65) Prior Publication Data

US 2009/0171196 A1 Jul. 2, 2009

(51) Int. Cl.
*A61B 6/00* (2006.01)

(52) U.S. Cl.
CPC .............. *A61B 90/96* (2016.02); *A61B 34/20* (2016.02); *A61B 90/39* (2016.02); *A61B 2090/3937* (2016.02); *A61B 2090/3983* (2016.02)

(58) Field of Classification Search
CPC .......... A61B 2019/442; A61B 19/5244; A61B 2019/5466; A61M 25/0108; A61M 25/01
USPC .............. 424/1.11, 1.25; 428/36.9, 375, 615; 600/393, 407, 411, 424, 426, 431; 604/529; 623/1.15, 1.34
See application file for complete search history.

(56) References Cited

U.S. PATENT DOCUMENTS

| | | | |
|---|---|---|---|
| 5,279,299 A * | 1/1994 | Imran | 600/393 |
| 5,345,936 A * | 9/1994 | Pomeranz et al. | 600/374 |
| 5,409,000 A | 4/1995 | Imran | |
| 5,944,712 A * | 8/1999 | Frassica et al. | 604/529 |
| 6,196,963 B1 * | 3/2001 | Williams | A61N 5/1007 600/3 |
| 6,370,421 B1 * | 4/2002 | Williams et al. | 600/433 |
| 6,556,695 B1 | 4/2003 | Packer et al. | |
| 7,263,397 B2 | 8/2007 | Hauck et al. | |
| 7,303,798 B2 * | 12/2007 | Bavaro et al. | 428/36.9 |
| 7,776,310 B2 * | 8/2010 | Kaplan | 424/1.25 |
| 7,840,254 B2 * | 11/2010 | Glossop | A61B 19/52 600/424 |
| 2002/0161421 A1* | 10/2002 | Lee | A61B 5/055 607/116 |

(Continued)

FOREIGN PATENT DOCUMENTS

| | | | | |
|---|---|---|---|---|
| WO | WO2005104951 | * | 11/2005 | A61B 6/00 |
| WO | WO2006016290 | * | 2/2006 | A61B 2090/392 |

OTHER PUBLICATIONS

International Search Report and Written Opinion for PCT/US2008/087131 mailed Feb. 6, 2009.

*Primary Examiner* — Serkan Akar
(74) *Attorney, Agent, or Firm* — Dykema Gossett PLLC (57) ABSTRACT

An imaging system comprises an image acquisition device configured to image certain internal anatomic structures of a patient, and an interventional device, at least a portion of which is configured to be inserted into the body of a patient. The interventional device includes one or more markers disposed on the insertable portion(s) of the interventional device. The material of which the marker is formed is suitable for detection by the image acquisition device, and is arranged in an identifying pattern. The image acquisition device is configured to detect the marker and to read the identifying pattern. In response to the detection and reading of the pattern, the image acquisition device is configured to identify and track the position of the interventional device.

9 Claims, 4 Drawing Sheets

(56) References Cited

U.S. PATENT DOCUMENTS

| | | | |
|---|---|---|---|
| 2002/0188194 A1* | 12/2002 | Cosman | 600/426 |
| 2003/0130576 A1* | 7/2003 | Seeley et al. | 600/426 |
| 2004/0073291 A1* | 4/2004 | Brown et al. | 623/1.15 |
| 2004/0109823 A1* | 6/2004 | Kaplan | 424/1.11 |
| 2004/0111149 A1* | 6/2004 | Stinson | 623/1.34 |
| 2005/0010300 A1* | 1/2005 | Disilvestro | A61F 2/32 623/18.12 |
| 2005/0049570 A1* | 3/2005 | Chin et al. | 604/500 |
| 2005/0064223 A1* | 3/2005 | Bavaro et al. | 428/615 |
| 2005/0064224 A1* | 3/2005 | Bavaro et al. | 428/615 |
| 2005/0065434 A1* | 3/2005 | Bavaro et al. | 600/424 |
| 2005/0080338 A1* | 4/2005 | Sirimanne et al. | 600/431 |
| 2005/0080339 A1* | 4/2005 | Sirimanne et al. | 600/431 |
| 2005/0085724 A1* | 4/2005 | Sirimanne et al. | 600/431 |
| 2005/0203384 A1* | 9/2005 | Sati et al. | 600/426 |
| 2005/0255317 A1* | 11/2005 | Bavaro et al. | 428/375 |
| 2006/0106375 A1* | 5/2006 | Werneth | A61B 18/1492 606/32 |
| 2006/0189896 A1* | 8/2006 | Davis et al. | 600/585 |
| 2007/0004981 A1* | 1/2007 | Boese et al. | 600/433 |
| 2007/0083102 A1* | 4/2007 | Pfister et al. | 600/407 |
| 2007/0100386 A1* | 5/2007 | Tronnes | A61N 1/3752 607/37 |
| 2007/0197905 A1* | 8/2007 | Timinger et al. | 600/424 |
| 2007/0299353 A1* | 12/2007 | Harlev | A61B 5/0422 600/509 |
| 2008/0021313 A1* | 1/2008 | Eidenschink et al. | 600/431 |
| 2008/0045827 A1* | 2/2008 | Rongen et al. | 600/407 |
| 2008/0119712 A1* | 5/2008 | Lloyd | 600/407 |
| 2008/0146942 A1* | 6/2008 | Dala-Krishna | 600/466 |
| 2008/0154120 A1* | 6/2008 | von Jako et al. | 600/411 |
| 2008/0267475 A1* | 10/2008 | Lendl | 382/130 |
| 2008/0287805 A1* | 11/2008 | Li | 600/471 |
| 2009/0162530 A1* | 6/2009 | Nesbitt | A61L 29/106 427/2.3 |
| 2009/0171196 A1* | 7/2009 | Olson et al. | 600/426 |
| 2009/0181156 A1* | 7/2009 | Nesbitt et al. | 427/2.1 |
| 2009/0216111 A1* | 8/2009 | Weese | A61B 6/12 600/424 |

* cited by examiner

METHOD AND APPARATUS FOR ENCODING CATHETERS WITH MARKERS FOR IDENTIFYING WITH IMAGING SYSTEMS

BACKGROUND OF THE INVENTION a. Field of the Invention

The present invention relates to imaging systems for use in the performance of medical diagnostic and therapeutic procedures. More particularly, the present invention relates to an imaging system comprising an interventional device configured to be inserted into the body of a patient and that includes one or more identifying markings to allow for its identification and tracking by the imaging system.

b. Background Art

A wide variety of imaging systems can be used to assist a clinician/physician in the performance of various medical diagnostic and therapeutic procedures relating to different parts of the human anatomy, such as, for example, the heart. Such imaging systems include, for example, those based on a variety of technologies, such as, fluoroscopy (i.e., x-rays), computed tomography (CT), magnetic resonance (MR), and intracardiac echocardiography (ICE). Among other things, these imaging systems may provide the ability to image and monitor the location of interventional devices disposed within the body of the patient and in the field of view of the imaging system, as well as, in certain instances, to assist in the navigation or guidance of these devices. Examples of interventional devices include, without limitation, various types of catheters, sheaths, intracardiac echocardiography devices, pacemaker leads, surgical implements, and the like. While the aforementioned systems may provide adequate means for the imaging, monitoring, and/or navigation or guidance of such devices, they are not without their drawbacks.

For instance, when a patient's heart is being imaged by an imaging system, image data corresponding to the imaged region is acquired. The acquired image data is then processed to generate an image/model of the imaged region. The generated image may then be subjected to additional processing techniques, such as, for example, real-time segmentation processes, in order to generate an image of a particular portion of the heart, and/or to locate/identify certain structures (e.g., anatomic structures, interventional devices, etc.) in two or three-dimensional space. When interventional devices of conventional construction are used, it is difficult, if not impossible, for the imaging system to accurately and sufficiently locate and/or identify the interventional device in the processed image, and therefore, the imaging system cannot easily identify the device or track its relative position. Further, when multiple interventional devices are being used and are present within the image generated by the imaging system, the imaging system cannot easily distinguish one device from another when the image is processed. Additionally, information relating to the interventional device (e.g., type, model, and/or other physical attributes of the device) cannot be easily obtained by the imaging system without system-operator interaction.

Accordingly, there is a need for an imaging system that will minimize and/or eliminate one or more of the above-identified deficiencies.

BRIEF SUMMARY OF THE INVENTION

The present invention is directed to an imaging system and the constituent components thereof. The imaging system comprises an image acquisition device configured to image certain structures within a patient's body, such as, for example anatomic structures and interventional devices. The imaging system further comprises an interventional device, at least a portion of which is configured to be inserted into the patient's body to perform various diagnostic and/or therapeutic procedures.

The interventional device of the present invention includes a marker disposed on the portion of the device that is configured to be inserted into the patient's body. The marker is formed of a material that can be detected by the image acquisition device, and is arranged in an identifying pattern so as to allow the image acquisition device to identify the interventional device encoded with the identifying pattern. Accordingly, the image acquisition device is configured to detect and read the pattern of the marker, and to then identify the device and also track its position within the patient's body.

In an exemplary embodiment, the interventional device can be encoded by performing a number of steps. First, an identifying pattern for the interventional device is selected. Second, a material that is suitable for detection by the image acquisition device is chosen. It is from the chosen material that the marker, and thus the identifying pattern, is formed. Finally, the identifying pattern is imposed on at least a portion of the interventional device.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
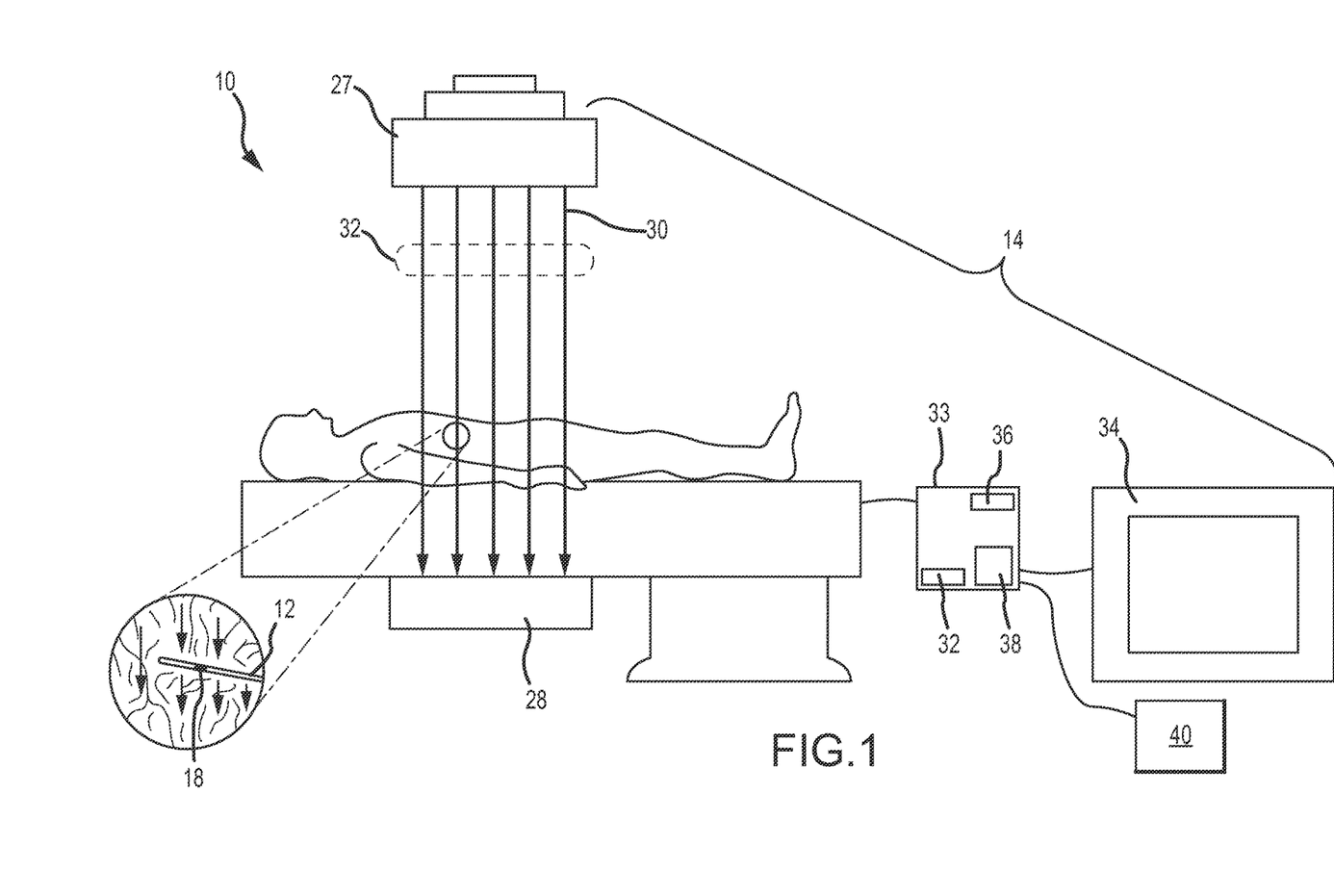
FIG. 1 is a diagrammatic view of an exemplary embodiment of an imaging system in accordance with the present invention showing an enlarged view of a portion of a patient's body.

Referring now to the drawings wherein like reference numerals are used to identify identical components in the various views, FIG. 1 illustrates an imaging system 10 in accordance with the present invention. Imaging system 10 is configured and operative to image desired internal anatomic structures of a patient and interventional devices proximate thereto, and may also be used to track and/or navigate the interventional devices. Accordingly, imaging system 10 may also be considered an "imaging and navigation" system rather than simply an "imaging" system. In the most general sense, imaging system 10 includes an interventional device 12 and an image acquisition device 14.

Figure 2:
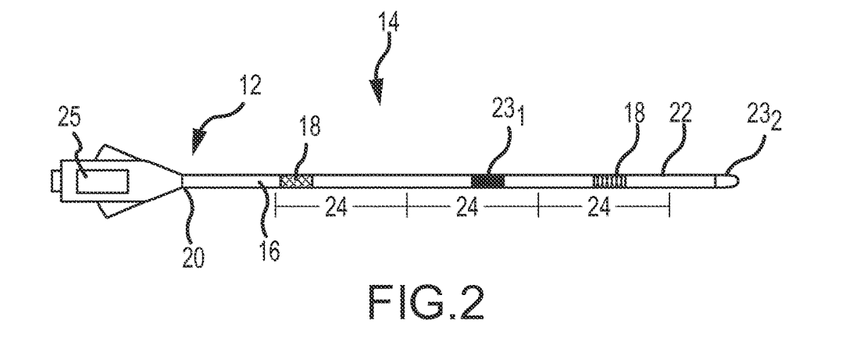
FIG. 2 is a diagrammatic view of an exemplary embodiment of an interventional device of the imaging system illustrated in FIG. 1.

FIG. 2 is a diagrammatic view of an exemplary embodiment of interventional device 12. Interventional device 12 includes at least one portion 16 that is configured for insertion into a patient's body (an insertable portion), and at least one marker 18 that is associated with portion 16. Portion 16 may be a rigid body, or alternatively, may be a deformable body (e.g., a the shaft of a catheter that may be deflected at one or more points in one or more directions, for example). As will be described in greater detail below, marker 18 is configured to allow image acquisition device 14 to identify interventional device 12 and monitor and/or track the location of portion 16 when it is disposed within the patient's body. For ease of description purposes, interventional device 12 will be described hereinafter as being a catheter, such as an electrophysiological (EP) catheter, and will be referenced as "catheter 12." Accordingly, portion 16, which corresponds to the elongated shaft of catheter 12, will hereinafter be referred to as "shaft 16." It should be noted, however, the present invention is not limited to interventional devices that take the form of a catheter. Rather, those of ordinary skill in the art will recognize that the present invention is equally applicable to other types of interventional devices, such as, for example, various types of catheters, sheaths, intracardiac echocardiography devices, pace maker leads, surgical implements, and the like.

In the exemplary embodiment illustrated in FIG. 2, shaft 16 has a proximal end 20 and a distal end 22. Shaft 16 may further include one or more electrodes 23 ($23_1, \ldots, 23_n$) coupled thereto that may be used for any number of diagnostic and/or therapeutic purposes. For instance, electrodes 23, and therefore, catheter 12, may be used for performing ablation procedures, cardiac mapping, electrophysiological (EP) studies, and other like procedures. Accordingly, the present invention is not limited to any one type of catheter or catheter-based procedure.

As briefly described above, catheter 12 further includes at least one marker 18 associated with shaft 16 at or near distal end 22 and in the vicinity of electrode(s) 23. In one embodiment, catheter 12 includes a single marker. However, in alternate exemplary embodiments, catheter 12 includes a plurality of markers 18 associated with shaft 16 at various locations thereof. The use of multiple markers provides a number of benefits/advantages. Among others, the use of multiple markers provides a measure of redundancy in case one marker is obscured by object, the ability to identify and track different portions or segments 24 of shaft 16 that have markers associated therewith, and, in certain instances, the ability to distinguish the segments 24 from each other.

Whether catheter 12 includes one or multiple markers, each marker 18 is formed of one or more materials that can be detected by image acquisition device 14, and that are shaped or arranged to form an identifying pattern. In an exemplary embodiment wherein catheter 12 includes multiple markers, the identifying pattern for each marker may be the same or, as will be described in greater detail below, each marker may have a different identifying pattern. In any event and in general terms, the identifying pattern allows for a certain degree of visualization and/or navigation of shaft 16. More specifically, the identifying pattern allows imaging system 10, generally, and image acquisition device 14, in particular, to detect and read marker 18 to identify catheter 12, monitor and track the position of shaft 16 (e.g., track the movement or orientation of shaft 16, or the rotation of shaft 16 about the longitudinal axis defined thereby), and/or assist a clinician/physician with navigation or guidance of shaft 16, and/or particular segments 24 thereof, with precision.

In one embodiment, marker 18 is formed of material that can be easily detected/imaged by image acquisition device 14 and distinguished from both electrodes 23 and shaft 16. However, because the electrodes may be detected/visualized by image acquisition device 14, in certain instances it may be beneficial or desirable to make one or more electrodes 23, or other elements associated with shaft 16, part of the identifying pattern, and therefore, marker 18. For example, as will be described in greater detail below, an interventional device having electrodes along with co-joining patterns identifiable by image acquisition device 14 has substantially ideal information that can be used in the registration of image acquisition device 14 with electric field based visualization, navigation, and mapping systems that may be a part of imaging system 10 or a separate and distinct system that works in conjunction with imaging system 10. An example of such a visualization, navigation, and mapping system is the EnSite NavX® system commercially offered by St. Jude Medical, Inc., which is described in detail in U.S. Pat. No. 7,263,397 entitled Method and Apparatus for Catheter Navigation and Location and Mapping in the Heart, issued to Hauck et al. and assigned to St. Jude Medical, Atrial Fibrillation Division, Inc., which is hereby incorporated by reference in its entirety. Similarly, interventional devices having magnetic sensors, for example, used for three-dimensional navigation purposes may have the sensors co-located in a known orientation or alignment with respect to marker(s) 18 and the identifying patterns thereof such that registration between the magnetic location system and imaging system 10 is facilitated. Thus, the material forming marker 18 may or may not necessarily need to be distinguishable from electrodes 23 or other elements associated with shaft 16.

In an exemplary embodiment, marker 18 is formed of a radiopaque material. However, the particular material used, radiopaque or otherwise, is dependent upon the type of imaging system being employed and the underlying technology upon which it is based. For instance, in one exemplary embodiment described in greater detail below, image acquisition device 14 is an x-ray based imaging system, and marker 18 is formed of one or more materials that are sufficiently radiopaque to be imaged using x-ray technology. In this embodiment, exemplary materials from which marker 18 may be formed include, without limitation, radiopaque compounds such as barium sulfate, bismuth trioxide, bismuth subcarbonate, bismuth oxychloride, and zirconium dioxide; and radiopaque metals such as tantalum, tungsten, gold, platinum, iridium, platinum-iridium, and stainless steel.

In alternate embodiments wherein imaging system 10 is not an x-ray based imaging system but rather is based on other technologies (e.g., CT, MR, ICE, ultrasound, etc.) that allow for either two- or three-dimensional image processing, marker 18 may be formed of one or more materials that have a radiopacity sufficient to allow for the imaging of marker 18 in the respective imaging technology. Additionally, in certain instances, such as MR or ultrasound imaging, for example, a material having a particular magnetic properties (for MR technologies) or varying abilities to reflect sound (for ultrasound technologies) would be used. Accordingly, the present invention is not limited to any one material from which marker 18 may be formed. Rather, depending on the imaging system used, marker 18 may be formed of any suitable material, radiopaque or otherwise, that will allow image acquisition device 14 to differentiate marker 18 from shaft 16 and electrodes 23, and also detect and read marker 18 to identify catheter 12 and monitor and track its position.

As described above, the material of marker 18 is arranged in an identifying pattern. The identifying pattern may be one of a predetermined or prescribed pattern, or a randomly generated pattern. In either instance, the identifying pattern allows, among other things, for catheter 12 to be differentiated or distinguished from other interventional devices (i.e., to facilitate, for example, monitoring and/or tracking of the particular devices), and may also allow image acquisition device 14 to determine and/or record a certain amount of information relating to the catheter. Additionally, in an embodiment wherein catheter 12 has multiple markers 18, the identifying patterns may allow for, among other things, the ability to track different segments 24 of shaft 16. Furthermore, when different identifying patterns are used for each marker, image acquisition device 14 may be able to identify and/or differentiate the particular segments 24 of shaft 16 from each other. For example, in an exemplary embodiment, the pattern of each marker has a first and a second portion. The first portion of each pattern is identical to the first portion of the other patterns. The second portion of each pattern, however, is unique to each respective pattern. Accordingly, while the first portion would allow image acquisition device 14 to recognize that each segment 24 of shaft 16 belongs to the same catheter 12, the second portion would allow image acquisition device 14 to identify and/or distinguish the respective segments 24 of catheter 12 marked with markers 18.

Figure 3A:
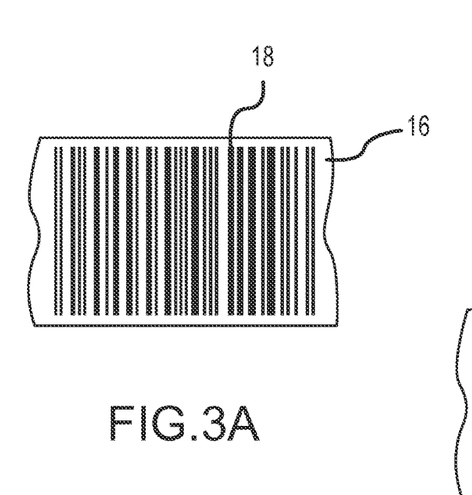
FIGS. 3A-3C are enlarged views of alternate embodiments of the identifying markers disposed on the interventional device illustrated in FIG. 2.
Figure 3B:
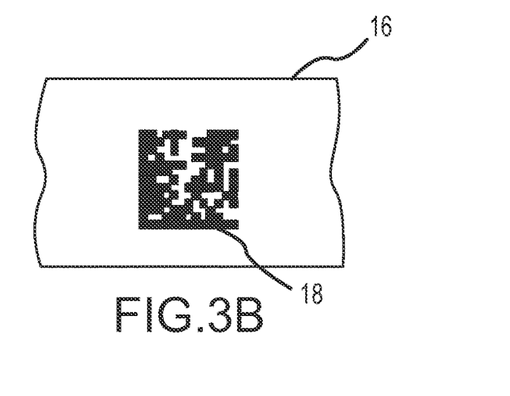
Figure 3C:
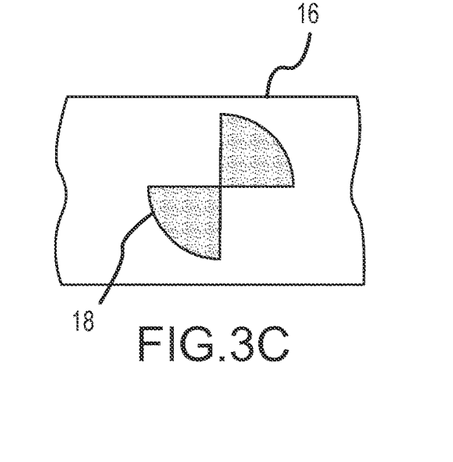

As briefly described above, the detectable material of which marker 18 is formed may be arranged in either prescribed or random patterns. Accordingly, in one exemplary embodiment, the material of marker 18 is arranged in a predetermined or prescribed pattern that is unique to the particular type/model of catheter in connection with which it is used. Therefore, because the prescribed pattern would be associated solely with a particular model/type of catheter, such an arrangement can be used to not only distinguish one catheter from another, but to also encode an identifier corresponding to certain attributes of catheter 12, such as, for example, the catheter's model and/or type, or information on various physical attributes thereof (e.g., the degree of flexibility of the shaft, the number, location, and/or type of electrodes, calibration information, etc.). Accordingly, as will be described in greater detail below, information relating to catheter 12 is associated with a specific serial number or other identifier. The serial number/identifier is then encoded in the form of a unique prescribed pattern. The pattern is then imposed or otherwise applied to catheter 12. Image acquisition device 14 is configured to detect marker 18, to read the prescribed pattern, and to extract/decode the serial number/identifier encoded in the identifying pattern. Image acquisition device 14 can then translate the serial number/identifier to obtain the specific information correlated with the identifier that relates to catheter 12. This information can then be used by image acquisition device 14 for a variety of purposes. FIGS. 3A-3C illustrate examples of prescribed patterns that may be used. These include bar codes similar to those used in retail applications (FIG. 3A), DataMatrix bar codes (FIG. 3B), predetermined patterns such as those used to track objects in automobile crash tests (FIG. 3C), pixilated dot patterns, and the like. It should be noted, however, that the present invention is not limited to just these illustrated examples. Rather, any predetermined or prescribed patterns that are known prior to fabrication of catheter 12 may be used.

In an alternate embodiment, the detectable material is arranged in a random pattern. In this embodiment, the pattern is randomly created and applied to shaft 16 during the fabrication process. The unique random arrangement may serve as a "fingerprint" for the particular catheter, which may be used by image acquisition device 14 to identify the catheter against all other devices and to differentiate or distinguish it therefrom. As will be described in greater detail below, image acquisition device 14 may be able to read the random pattern and record it and/or certain information relating to the catheter marked with the random pattern. Image acquisition device 14 may then use this information to later correlate the pattern with a specific device or for various other purposes.

In an exemplary embodiment, a part of the aforementioned fabrication process of catheter 12 includes recording an identifier corresponding to catheter 12 in a memory device 25. Such an identifier may include, for example, the particular random pattern applied to shaft 16, traits or characteristics of catheter 12, a serial number, or any other like identifiers. Memory device 25 may take the form of any number of memory devices including, without limitation, a static random access memory (SRAM), an electrically erasable programmable read-only memory (EEPROM or E2PROM), or any other suitable device. In one embodiment, memory device 25 is included as part of catheter 12. More specifically, memory device 25 may be packaged with catheter 12 such as, for example, in the handle portion or connector thereof. However, in alternate embodiments, memory device 25 may be disposed elsewhere within the catheter assembly or separate therefrom.

When catheter 12 having memory device 25 is connected to imaging system 10, memory device 25 can be read and the information recorded thereon may be used by system 10 for a variety of purposes. One such purpose is to identify catheter 12 and/or various characteristics thereof. When either the pattern imposed on shaft 16 or another identifier (e.g., serial number) corresponding to catheter 12 is recorded in memory device 25, system 10 is able to read the pattern/identifier from memory device 25 and then look it up in a database or look-up table that is either part of system 10 or that is external thereto but accessible thereby. The database/look-up table contains a collection or list of patterns and/or identifiers, as the case may be, corresponding to various interventional devices, as well as information relating to the catheter/interventional device associated with each pattern/identifier. This information may include, for example, the type or model of the device (e.g., catheter for ablation, catheter for ultrasound based procedure, catheter for performing electrophysiological studies and mapping, etc.) and/or particular properties/attributes of the device. Accordingly, once system 10 reads the pattern/identifier from memory device 25, it can translate it by looking it up in database and correlating the information corresponding to the particular pattern/identifier with catheter 12. This allows imaging system 10 to know particular details relating to the interventional device, and thus, to identify the device with specificity. This information may then be stored in a memory that is part of or external to imaging system 10, displayed on a display of imaging system 10, or for other purposes.

Another, and somewhat related, use of the information recorded in memory device 25 is that it may provide the ability to inform imaging system 10 that the catheter corresponding to the recorded information (e.g., the pattern, identifier, specific information, etc.) is being used, and to prompt imaging system 10 to try to locate the particular catheter.

In the instance where the pattern itself is recorded in memory device 25, to record the pattern the portion of the catheter comprising the pattern is imaged using, for example, imaging system 10 or another imaging system. Once this image is generated, it is recorded in memory device 25. In the instance where an identifier corresponding to catheter 12 or specific information relating to catheter 12 is recorded in memory device 25, the identifier/information may be recorded on memory device 25 by programming memory device 25.

It should be noted that while the above described recordation process finds particular applicability with respect to randomly generated patterns, the present invention is not meant to be so limited. Rather, identifiers corresponding to catheters encoded with prescribed patterns may also be stored in a memory device associated with the catheter. Accordingly, prescribed patterns be imaged and stored in a memory device of the catheter and may be used by imaging system 10 for a variety of purposes. Therefore, this aspect of the present invention is not meant to be limited solely to catheters having random patterns imposed thereon.

Whether the pattern of marker 18 is prescribed or random, countless numbers of patterns may be suitable for use. In order to simplify the identification of the location of marker 18 and the detection/reading of its pattern by image acquisition device 14, in an exemplary embodiment, the pattern is one unlikely to occur naturally in anatomic structures. Accordingly, because anatomic structures do not typically have sharp edges/boundaries, patterns having relatively sharp boundaries may be desirable. When marker 18 comprises such patterns, known image processing techniques/algorithms, such as, for example, fast-fourier transforms (FFTs), may be used to easily filter the image acquired by image acquisition device 14 to remove the background and leave only the pattern imposed on catheter 12. This allows image acquisition device 14 to easily detect and read marker 18. It should be noted, however, that while it may be desirable to have patterns not likely to occur in anatomic structures, the present invention is not meant to be so limited. Accordingly, patterns of any number of shapes and sizes may be used to create marker 18.

Figure 4:
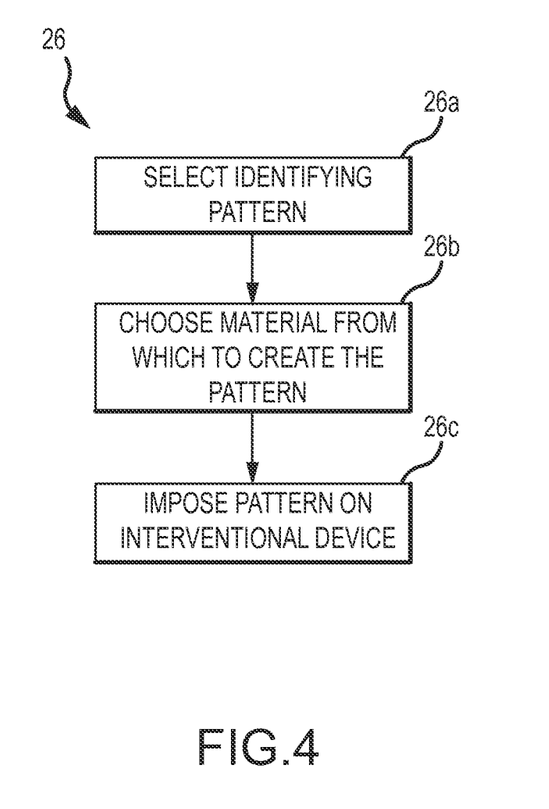
FIG. 4 is a flow diagram illustrating an exemplary method of encoding an interventional device in accordance with the present invention.

Numerous methods may be employed to "encode" or otherwise associate marker 18 with shaft 16. FIG. 4 illustrates one such exemplary method 26. In a first step 26*a*, the identifying pattern that will allow image acquisition device 14 to identify and track catheter 12 must be selected. In an exemplary embodiment, the selection of the identifying pattern includes selecting one of a prescribed pattern or a random pattern. In a second step 26*b*, the type of detectable material to be used to create the selected identifying pattern, including, without limitation, those specifically identified above, must be chosen. Finally, in third step 26*c*, the identifying pattern is imposed on or in a portion of shaft 16, thereby creating marker 18. In one exemplary embodiment, the imposition of the identifying pattern includes forming shaft 16 of a polymeric material and doping the polymeric material with the detectable material. In an alternate embodiment, however, the imposition of the identifying pattern includes embedding one or more discrete components formed of the detectable material in shaft 16.

Referring back to FIG. 1, image acquisition device 14 will now be described in greater detail. As briefly described above, image acquisition device 14 is configured to image desired anatomic structures of a patient, such as the heart, as well as interventional devices, such as catheters, that may be disposed within the patient. As also described above, image acquisition device 14 may take the form of any number of image acquisition devices/technologies. In an exemplary embodiment, image acquisition device 14 utilizes x-ray based technology such as fluoroscopy. In alternate embodiments, image acquisition device 14 may take on one or more other two-dimensional or three-dimensional imaging technologies including, without limitation, computed tomography (CT), magnetic resonance (MR), and intracardiac echocardiography (ICE). Accordingly, the present invention is not limited to one particular type of imaging technology. However, for ease of description purposes alone, image acquisition device 14 will be described hereinafter only as an x-ray based fluoroscopic device/system.

Image acquisition device 14 is configured to acquire image data relating to particular structures (e.g., anatomic structures, interventional devices, etc.) disposed within the body of the patient. Using various techniques and software, the acquired image data can be processed and a model of desired structures can be generated in substantially real-time. In an exemplary embodiment, image acquisition device 14 includes a radiation source 27 and a screen or sensor 28 that is spaced apart from radiation source 27 by a distance sufficient to allow a typical size range of human patients to be positioned therebetween. Image acquisition device 14 further includes a field of view 32 that defines the boundaries of the area of the patient that is ultimately imaged. For purposes of explanation and illustration only, field of view 32 is illustrated in FIG. 1 as being defined by the emissive range of radiation source 27, however, the present invention is not limited to such a configuration. Radiation source 27 is configured to direct x-rays 30 toward sensor 28. Generally speaking, as x-rays 30 either pass through or are alternatively absorbed in varying degrees by anatomic structures in the patient's body, an image revealing the constituent anatomic structure of the imaged region is created on screen/sensor 28. The x-rays 30 may also reveal the presence and location of interventional devices disposed within the imaged region, such as one or more catheters, in the same manner.

Image acquisition device 14 may further include a processing unit 33 that is electrically connected to sensor 28. Processing unit 33 is configured to, among other things, receive the image data acquired by image acquisition device 14 and to process the data using various software and imaging techniques or image processing to generate one or more desired images of the structure(s) represented by the data. Processing unit 33 may be further configured to perform additional processing on the generated image (i.e., the image data corresponding to the generated image) to allow for images of particular regions of an imaged structure to be generated. For example, image acquisition device 14 may include software configured to perform various image processing techniques, such as real-time segmentation, on the generated image. Such processing allows, among other things, image acquisition device 14 to locate and identify particular imaged structures (e.g., anatomic structures, interventional devices, etc.), or portions thereof, in two or three dimensional space.

Image acquisition device 14 may further include a monitor 34 that is electrically connected to processing unit 33. Accordingly, once the image data is processed and a corresponding image is generated, it may be communicated to monitor 34 for display. In addition to providing an image of the desired anatomic structure, monitor 34 may also provide a clinician/physician the ability to guide interventional devices, such as one or more catheters 12, disposed within the patient in field of view 32 of image acquisition device 14. While in the above-described embodiment processing unit 33 and monitor 34 are part of image acquisition device 14, the present invention is not so limited. Rather, in alternate embodiments, one or both of processing unit 33 and monitor 34 may be electrically connected to image acquisition device 14, but may be separate and distinct components of imaging system 10. Additionally, it should be noted that while processing unit 33 and monitor 34 may be used to perform some or all of the aforementioned processing and to display the results of this processing, in alternate embodiments, the processing tasks may be divided and another processing unit or workstation, for example, may be used to perform some or all of the requisite processing. For example, processing unit 33 may be configured to perform image reconstruction of a modeled structure, but the automatic image segmentation and catheter tracking may be processed elsewhere in the system and be displayed on a separate display device. Accordingly, the present invention is not limited to the arrangement of processing unit 33 and display 34 illustrated in FIG. 1, but rather alternate arrangements and configurations of processing unit 33 and display 34 remain within the spirit and scope of the present invention.

In addition to the functionality described above, image acquisition device 14 is further configured to detect and/or read the markers disposed on each interventional device. As described above, since fluoroscopy is an x-ray based imaging technology/system, in an exemplary embodiment, marker 18 comprises a radiopaque material that becomes visible under exposure to x-rays. Accordingly, image acquisition device 14 is configured to detect marker 18 using various imaging software/algorithms (e.g., FFTs), and to read and/or decode the particular pattern of marker 18 using pattern recognition algorithms (i.e., varying light and dark portions of the particular pattern generate a region of high-frequency in the image, making it easy for image processing algorithms to detect and read the patterns) or other software applications. A wide variety of detection and pattern recognition algorithms or techniques are generally known to those of ordinary sill in the art and any number of them may find utility or application in this invention. In light of the fact that these techniques are known, a detailed description of these techniques will not be provided. The detection and reading of marker 18, and its identifying pattern, in particular, provides a number of benefits and/or may serve a number of purposes.

One such benefit or purpose is that by detecting and/or reading the pattern of marker 18, image acquisition device 14 is able to automatically identify each catheter or other interventional devices having an identifying marker. Further, because each marked device is identified, image acquisition device 14 is able to at least detect the presence of catheter 12 and differentiate or distinguish it from other interventional devices that may be disposed within the image. This functionality eliminates, or at least substantially reduces, the chance of misidentifying the devices in the processed image. Accordingly, by detecting and/or reading markers 18, image acquisition device 14 is able to identify, with particularity, each device, and, if appropriate, to distinguish each device from others disposed within an image.

Another related benefit or purpose is realized when, as described above, the material forming marker 18 is arranged in a prescribed pattern so as to encode catheter 12 with particular information relating to catheter 12. In this instance, because image acquisition device 14 is capable of detecting and reading the identifying pattern, in addition to generally identifying catheter 12 and distinguishing it from other detected catheters/interventional devices, image acquisition device 14 is able to automatically identify certain attributes/details of catheter 12. More specifically, image acquisition device 14 may include or have access to a look-up table or database 36 containing a list of serial numbers or identifiers corresponding to various interventional devices, as well as information relating to the catheter/interventional device associated with each serial number/identifier. This information may include, for example, the type or model of the device (e.g., catheter for ablation, catheter for ultrasound based procedure, catheter for performing electrophysiological studies and mapping, etc.) and/or particular properties/attributes of the device. Accordingly, as previously described, once image acquisition device 14 detects marker 18 and reads its identifying pattern, it can decode the identifying pattern to extract a serial number or other identifier. Once image acquisition device 14 has extracted the serial number/identifier, it can translate it by looking it up in database 36 and correlating the information corresponding to the particular identifier with catheter 12. This allows image acquisition device 14 to know particular details relating to the interventional devices disposed within an image, and thus, to identify the respective devices with specificity. Additionally, the information may also be stored in a storage medium 38 for later retrieval and use, or displayed, in whole or in part, on display 34. One or both of database 36 and storage medium 38 may be located within processing unit 33, or alternatively may be separate and distinct from processing unit 33. In addition, database 36 and/or storage medium 38 may be separate and distinct components of imaging system 10, and thus, separate and distinct from image acquisition device 14 altogether.

Similar to the prescribed pattern described immediately above, when the detectable material is arranged in a random pattern, image acquisition device 14 may detect and read the random pattern and record it in storage medium 38, for example, with a unique identification number (e.g., serial number) for later retrieval and use. Among other things, this serial number may then be used, for example, to correlate the device encoded with the random pattern with a specific device. As with any pattern, the random pattern also allows image acquisition device 14 to distinguish the particular catheter associated with the detected random pattern from other detected catheters/interventional devices in an image.

Yet another benefit or purpose is that by detecting marker 18, and irrespective of whether the identifying pattern is prescribed or random, image acquisition device 14 is able to determine the relative position of catheter 12. Once the relative location of catheter 12 is known (i.e., the reference coordinates of marker 18 within the particular image), image acquisition device 14 may track its position within the image. Accordingly, when the ability to detect/read marker 18 is combined with image processing techniques that allow for the locating and identification of structures in two or three-dimensional space, catheter 12 can be identified and its position and orientation tracked relative to both the imaged anatomic structure and other interventional devices that may be in the image. For example, in an embodiment wherein image acquisition device 14 is a bi-plane fluoroscopy system, catheter 12 can be tracked in two views, and thus, three-dimensional position information of catheter 12 can be generated and provided to image acquisition device 14.

Therefore, to summarize, image acquisition device 14 is configured to detect marker 18, and to read the specific pattern thereof. Once marker 18 is detected and read, image acquisition device 14 is able to identify the device and differentiate or distinguish it from other devices within the same image. Additionally, image acquisition device 14 may be able to determine specific information relating to the identified device. Finally, once marker 18 is detected, image acquisition device 14 is able to determine to relative position of the device, and may then track or monitor its position within the image.

While the detailed description set forth above is focused primarily on the use of interventional devices marked with identifying patterns in an "imaging system," those of ordinary skill in the art will recognize and appreciate that the principles and features described above may find application or use in a variety of other types of systems that are used for a variety of purposes. Accordingly, those of ordinary skill in the art will appreciate that when one or more markers 18 comprising identifying patterns are associated with catheter shaft 16 and can be detected/read by image acquisition device 14, catheter 12 and image system 10 as a whole may be used to perform any number of procedures/functions. For instance, because the location and position of each catheter/interventional device can be automatically tracked by image acquisition device 14, imaging system 10 may be used to perform various mapping functions of a particular anatomic structures (e.g., the mapping of electrical activity in a chamber of the heart), various physiological and electrophysiological studies, and other similar functions either in conjunction with or without known navigation and visualization systems and their constituent components.

For example, as briefly described above, imaging system 10 may include or be used in conjunction with a visualization, navigation, and mapping system such as the EnSite NavX® system referred to above. Such systems have the capability to, among other things, generate models of anatomic structures, present or display information (e.g., electrophysiological data) relating to the modeled structure, and/or perform other EP procedures. In these systems, interventional devices are typically located and tracked using a methodology involving electric fields. Generally speaking, these systems include two or more external patient electrode patches that are applied to the patient's body at two or more locations. An electrical signal is transmitted between the patches to generate an electric field, and one or more electrodes of one or more catheters within the heart sense the signal. The system collects electrical data from the catheter(s) and uses it to track the catheter(s) movement and to construct or generate models of one or more desired structures. Additionally, a physician may sweep the catheter(s) across an anatomic structure such as a heart chamber during data collection to outline the structures and relay the signals to a computer system thereof, which generates the desired model. The resulting model may then be used, for example, to guide interventional devices to one or more locations in or around the heart (or other anatomic structure) where treatment or investigation is needed. These systems may be further used, for example, to catalog places of treatment (e.g., ablation) and to correlate location information with sensed electrical information. These and other processes, methods, techniques, and features of such systems are described in greater detail in U.S. Pat. No. 7,263,397 referenced above, which has been incorporated herein by reference.

Figure 5:
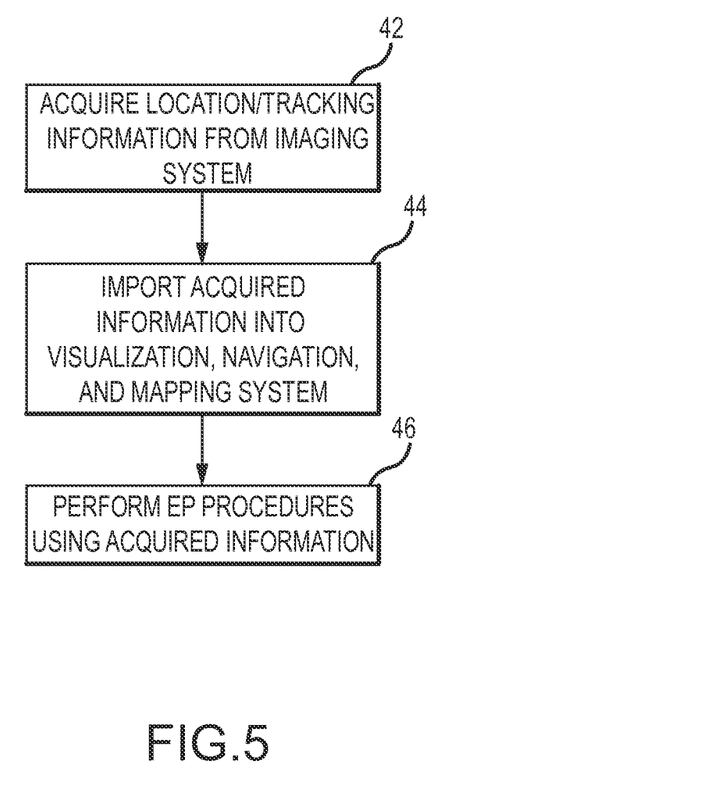
FIG. 5 is a flow diagram illustrating an exemplary method of presenting cardiac medical information in accordance with the present invention.

Accordingly, with reference to FIGS. 1 and 5, imaging system 10 includes a visualization, navigation, and mapping subsystem 40. Alternatively, rather than being part of imaging system 10, subsystem 40 may be a separate and distinct system that is used in conjunction with imaging system 10. In either case, the interventional device location/tracking capabilities of imaging system 10 (i.e., image acquisition 14) that are described in great detail above may be combined with the mapping and model generation functionality, for example, of a visualization, navigation, and mapping subsystem 40 to provide these systems with an alternate way of navigating and tracking interventional devices. Thus, in one embodiment, the methodology described above for identifying and tracking catheters marked with identifying patterns is used to acquire substantially real-time location information relating to catheter 12 (step 42). This information is then imported or fed into visualization, navigation, and mapping subsystem 40 (step 44). Once the location information is imported, subsystem 40 may use it to track and/or navigate catheter 12 and to assist in the performance of various EP procedures/functions (step 46). Therefore, in this embodiment, imaging system 10, and image acquisition device 14, in particular, provides an alternate way of locating and tracking interventional devices compared to the electric field techniques typically employed in these systems. Accordingly, the need for electrode patches and other related required components is negated.

Further, because particular segments 24 of catheter 12 may be precisely located and tracked, it is also possible to represent catheter 12 as a spline, which may allow for efficient importation or representation in other imaging/navigation systems, such as subsystem 40.

Additionally, in alternate embodiments, images acquired by image acquisition device 14 may be registered otherwise integrated or merged with subsystem 40. A detailed description of exemplary methods for carrying out such integration or merging of images can be found in U.S. Pat. No. 6,556,695 entitled Method for Producing High Resolution Real-Time Images, of Structure and Function During Medical Procedures, issued to Packer et al. and assigned to Mayo Foundation for Medical Education and Research, which is hereby incorporated by reference in its entirety.

Although only certain embodiments of this invention have been described above with a certain degree of particularity, those skilled in the art could make numerous alterations to the disclosed embodiments without departing from the spirit or scope of this invention. For example, interventional devices other than catheter 12 may include markers 18 to serve the same purpose as that described above with respect to catheter 12. Further, marker 18 may be constructed of any number and/or types of detectable materials, and the detectable materials may be arranged in any number of patterns. Still further, while image acquisition device 14 has been described in detail with respect to x-ray based imaging technologies, in reality, image acquisition device 14 may take the form of various other types of imaging technologies, including three-dimensional image processing technologies. Additionally, joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system comprising:
   an image acquisition device having a field of view; and
   an interventional device, wherein the interventional device is a catheter, and wherein the interventional device comprises:
      a portion configured for insertion into the body of a patient, and
      a marker disposed on said portion, said marker formed of a material that can be detected by said image acquisition device, wherein the material is arranged in an identifying pattern, wherein the identifying pattern encodes a serial number of the interventional device and encodes information associated with a number of electrodes disposed on a shaft of the catheter and a location of the electrodes disposed on the shaft of the catheter, wherein the identifying pattern and the serial number are configured to be identified by the image acquisition device while the interventional device is in the body of the patient and the identifying pattern is formed of a material that is distinguishable from the shaft and the electrodes by the image acquisition device, and wherein the identifying pattern is configured to be tracked by the image acquisition device upon identification of the identifying pattern and the serial number with the image acquisition device;

wherein said image acquisition device is configured to read said identifying pattern, while said marker is disposed inside a body of a patient, to identify a serial number of said interventional device based on said identifying pattern, to identify the number of electrodes and location of the electrodes disposed on the shaft based on the identifying pattern, and to identify certain attributes of said interventional device based on said identifying pattern.

2. The system in accordance with claim 1 wherein said image acquisition device is an x-ray based image acquisition device, and said material is a radiopaque material.

3. The system in accordance with claim 1 wherein said image acquisition device is configured to read said identifying pattern and to correlate said identifying pattern with interventional device data stored in a database associated with said image acquisition device.

4. The system in accordance with claim 1 wherein said portion of said interventional device comprises a plurality of segments and each of said segments includes a marker associated therewith, and further wherein said image acquisition device is configured to identify and track each of said plurality of segments.

5. The system in accordance with claim 1 wherein said interventional device further comprising a memory device configured for storing an identifier corresponding to said interventional device and to provide said stored identifier to said image acquisition device.

6. The system in accordance with claim 1 wherein said image acquisition device is configured to generate location information corresponding to said interventional device based on the detection of said identifying pattern, said system further comprising a mapping subsystem that is electrically connected to said image acquisition device and configured to receive said location information from said image acquisition device, said mapping subsystem further configured to generate a model of a desired anatomic structure and to display electrophysiological data corresponding to said structure on said model based on said location information.

7. The system in accordance with claim 1 wherein said image acquisition device is configured to track the orientation of said interventional device.

8. The system in accordance with claim 1 wherein said image acquisition device is configured to track the motion of said interventional device.

9. The system in accordance with claim 1 wherein said insertable portion of said interventional device comprises a catheter shaft defining a longitudinal axis, and said image acquisition device is configured to track rotation of said catheter shaft about said longitudinal axis.

* * * * *